United States Patent
Legrand et al.

(10) Patent No.: US 6,569,677 B1
(45) Date of Patent: May 27, 2003

(54) MODIFIED ADENOVIRAL FIBER AND TARGET ADENOVIRUSES

(75) Inventors: Valérie Legrand, Strasbourg (FR); Majid Mehtali, Illkirch Graffenstaden (FR); Pierre Boulanger, Montpellier (FR)

(73) Assignees: Transgene S.A., Strasbourg (FR); Centre National de la Recherche Scientifique (CNRS), Paris (FR)

(*) Notice: Subject to any disclaimer, the term of this patent is extended or adjusted under 35 U.S.C. 154(b) by 0 days.

(21) Appl. No.: 09/402,401

(22) PCT Filed: Apr. 2, 1998

(86) PCT No.: PCT/FR98/00668

§ 371 (c)(1), (2), (4) Date: Oct. 4, 1999

(87) PCT Pub. No.: WO98/44121

PCT Pub. Date: Oct. 8, 1998

(30) Foreign Application Priority Data

Apr. 2, 1997 (FR) ............................................. 97 03987
Apr. 17, 1997 (FR) ............................................. 97 04747

(51) Int. Cl.$^7$ ........................ C12N 15/861; C12N 15/86
(52) U.S. Cl. ................. 435/320.1; 435/91.4; 424/93.2; 514/44
(58) Field of Search ...................... 424/93.2; 435/320.1, 435/91.4; 514/44

(56) References Cited

U.S. PATENT DOCUMENTS 5,543,328 A    8/1996  McClelland et al.

FOREIGN PATENT DOCUMENTS

| FR | 94 14470 | 6/1996 | |
|---|---|---|---|
| WO | 94/17832 | 8/1994 | |
| WO | WO94/28152 | 12/1994 | |
| WO | 95/05201 | 2/1995 | |
| WO | WO95/16048 | 6/1995 | |
| WO | 95/26412 | 10/1995 | |
| WO | WO95/26412 | 10/1995 | |
| WO | WO 96/13597 | 5/1996 | * |
| WO | 96/26281 | 8/1996 | |
| WO | WO96/26281 | 8/1996 | |

OTHER PUBLICATIONS

Krasnykh et al.; Generation of Recombinant Adenovirus Vectors with Modified Fibers for Altering Viral Tropism, 1996, Journal of Virology : 6839–6846.*
Hong et.al.; Domains Required for Assembly of Adenovirus Ttpe 2 Fiber Trimers, 1996, Journal of Virology: 7071–7078.*
Gall et.al.; Adenovirus Type 5 and 7 CApsid Chimera: Fiber Replacement Alters Receptor Tropism without Affecting Primary Immune Neutralization Epitopes, 1996, Journal Of Virology: 2116–2123.*

J. Gall et al., Journal of Virology, 70(4):2116–2123 (1996).
A. McClelland et al., Journal of Cellular Biochemistry—Supplement, p. 411 (1995).
Bramson et al, 1995, Curr. Op. Biotech. 6, 590–595.
Graham et al, 1977, J. Gen. Virol. 36, 59–72.
Philipson et al, 1968, J. Virol. 2, 1064–1075.
Defer et al, 1990, J. Virol. 64, 3662–3673.
Mathias et al, 1994, J. Virol. 68, 6811–6814.
Chroboczek et al, 1995, Current Top. Microbiol. Immunol. 199, 165–200.
Hong and Engler, 1996, J. Virol. 70, 7071–7078.
Novelli and Boulanger, 1991, J. Biol. Chem. 266, 9299–9303.
Novelli and Boulanger, 1991, Virology 185, 365–376.
Henry et al, 1994, J. Virol. 68, 5239–5246.
Louis et al, 1994, J. Virol. 68, 4104–4106.
Bergelson et al, 1997, Science 275, 1320–1323.
Herisse et al, 1981, Nucleic Acid Res. 9, 4023–4042.
Chronboczek and Jacrot, 1987, Virology 161, 549–554.
Xia et al, 1994, Structure 2, 1259–1270.
Stryer, Biochemistry, $2^{nd}$ edition, Chapter 2, pp. 11–39, Ed. Freeman and Co., San Francisco.
Fawell et al, 1994, Proc. Natl. Acad. Sci. USA 91, 664–668.
Michael et al, 1995, Gene Therapy 2, 660–668.
Felgner et al, 1989, Proc. West. Pharmacol. Soc. 32, 115–121.
Hodgson and Solaiman, 1996, Nature Biotechnology 14, 339–342.
Remy et al, 1994, Bioconjugate Chemistry 5, 647–654.
Roelvink et al, 1996 J. Virol. 70, 7614–7621.
Gooding and Wold, 1990, Critical Reviews of Immunology 10, 53–71.
Ensinger et al, 1972, J. Virol. 10, 328–339.
Ido et al, 1995, Cancer Res. 55, 3105–3109.
Lee et al, 1996, J. Biol. Chem. 271–4561–4568.
Morishita et al, 1995, J. Biol. Chem. 270, 27948–27953.
Graham and Prevec, 1991, Methods in Molecular Biology, vol. 7, p. 109–128; Ed. E.J. Murray, The Human Press, Inc.
Hubacek and Glover, 1970, J. Mol. Biol. 50, 111–127.
Hanahan, 1983, J. Mol. Biol. 166, 557–580.
PCR Protocols–A–Guide to Methods and Application, 1990, edited by Innis, Gelfand, Sninsky and White, Academic Press, Inc.

(List continued on next page.)

Primary Examiner—Scott D. Priebe
(74) Attorney, Agent, or Firm—Burns, Doane, Swecker & Mathis, L.L.P.

(57) ABSTRACT

The invention relates to an adenovirus fiber modified by the mutation of one or more residues. The residues are directed towards the natural cell receptor in the three-dimensional structure of said adenovirus. The invention further relates to a DNA fragment, and expression vector, and a cell line expressing said fiber, and also concerns an adenovirus, the process for producing this type of adenovirus, and a infectable host cell, as well as their therapeutic application and a corresponding pharmaceutical composition.

10 Claims, No Drawings

OTHER PUBLICATIONS

Wells et al, 1990, Science 247: 962–964.
Schneider et al, 1986, Proc. Natl. Acad. Sci. USA 83, 333–336.
Quillet et al, 1988, J. Immunol. 141, 17–20.
Kieny et al, 1983, Gene 26, 91–99.
Chartier et al, 1996, J. Virol. 70, 4805–4810.
Zachary et al, 1985, Proc. Natl. Acad. Sci. USA 82, 7616–7620.
Battey et al, 1991, Proc. Natl. Acad. Sci. USA 88, 395–399.
Corjay et al, 1991, J. Biol. Chem 266, 18771–18779.
Stratford–Perricaudet et al, 1992, J. Clin. Invest. 90, 626–630.
Boshat et al, 1985, Cell 41, 521–530.

* cited by examiner

MODIFIED ADENOVIRAL FIBER AND TARGET ADENOVIRUSES

The subject of the present invention is an adenoviral fiber mutated in the regions involved in the recognition and the binding of the natural cell receptor for adenoviruses. It also relates to the recombinant viruses carrying at their surface such a fiber and a ligand which confers on them a modified or targeted host specificity towards a particular cell type, the cells containing these adenoviruses as well as a method for preparing infectious viral particles thereof intended for therapeutic use. The invention is most particularly of interest for gene therapy perspectives, in particular in humans.

By virtue of their particular properties, adenoviruses are used in an increasing number of applications in gene therapy. Having been identified in numerous animal species, they are not very pathogenic, are nonintegrative and replicate both in dividing and quiescent cells. Furthermore, they exhibit a broad host spectrum and are capable of infecting a very large number of cell types such as epithelial cells, endothelial cells, myocytes, hepatocytes, nerve cells and synoviocytes (Bramson et al., 1995, Curr. Op. Biotech. 6, 590–595). However, this absence of specificity of infection could constitute a limit to the use of recombinant adenoviruses, on the one hand, from a safety point of view since there may be dissemination of the recombinant gene in the host organism and, on the other hand, from the efficiency point of view since the virus does not infect specifically the cell type which it is desired to treat.

In general, the adenoviral genome consists of a double-stranded linear DNA molecule of about 36 kb containing the genes encoding the viral proteins and, at its ends two inverted repeats (designated ITR for Inverted Terminal Repeat) involved in the replication and the encapsidation region. The early genes are distributed in 4 regions dispersed in the adenoviral genome (E1 to E4; E for early), containing 6 transcriptional units equipped with their own promoters. The late genes (L1 to L5; L for late) partly cover the early transcription units and are, for the most part, transcribed from the major late promoter MLP.

As a guide, all the adenoviruses used in gene therapy protocols are deficient for replication by deletion of at least the E1 region and are propagated in a complementation cell line which provides in trans the deleted viral functions. The 293 line, established from human embryonic kidney cells, which efficiently complements the E1 function (Graham et al., 1977, J. Gen. Virol. 36, 59–72), is commonly used. Second-generation vectors have recently been proposed in the literature. They conserve the regions in cis which are necessary for the replication of the virus in the infected cell (ITRs and encapsidation sequences) and contain substantial internal deletions designed to eliminate most of the viral genes whose expression in vivo can lead to the establishment of inflammatory or immune responses in the host. The adenoviral vectors and the technique for their preparation have been the subject of numerous publications which are accessible to persons skilled in the art.

The infectious cycle for adenoviruses occurs in 2 steps. The early phase precedes the initiation of replication and makes it possible to produce the early proteins regulating the replication and transcription of the viral DNA. The replication of the genome is followed by the late phase during which the structural proteins which constitute the viral particles are synthesized. The assembly of the new virions takes place in the nucleus. In a first stage, the viral proteins assemble so as to form empty capsids of icosahedral structure into which the genome is encapsidated. The adenoviruses liberated are capable of infecting other permissive cells. In this regard, the fiber and the penton base present at the surface of the capsids play a critical role in the cellular attachment of the virions and their internalization.

The adenovirus binds to a cellular receptor present at the surface of the permissive cells via the trimeric fiber (Philipson et al., 1968, J. Virol. 2, 1064–1075; Defer et al., 1990, J. Virol. 64, 3661–3673). The particle is then internalized by endocytosis through the binding of the penton base to the cellular integrins $\alpha_v\beta_3$ and $\alpha_v\beta_5$ (Mathias et al., 1994, J. Virol. 68, 6811–6814). The capacity of the soluble fiber or of anti-fiber antibodies to inhibit infection demonstrates its role in the cellular attachment of the virus.

The fiber is composed of 3 domains (Chroboczek et al., 1995, Current Top. Microbiol. Immunol. 199, 165–200):
(1) At the N-terminus, the tail, which is highly conserved from one serotype to another, interacts with the penton base and ensures the anchorage of the molecule in the capsid.
(2) The stem is a structure in the form of a rod, composed of a number of repeats of $\beta$ sheets, this number varying depending on the serotypes.
(3) Finally, at the distal end of the stem, the head is a spherical globular structure which contains the trimerization signals (Hong and Engler, 1996, J. Virol. 70, 7071–7078; Novelli and Boulanger, 1991, J. Biol. Chem. 266, 9299–9303; Novelli and Boulanger, 1991, Virology 185, 365–376). Furthermore, most of the experimental data show that the head domain is responsible for the binding to permissive cells (Henry et al., 1994, J. Virol. 68, 5239–5246; Louis et al., 1994, J. Virol. 68, 4104–4106).

"Targeted" adenoviruses whose native fiber is modified so as to recognize a different cellular receptor have already been proposed in the literature. Thus, WO94/10323 describes mutants of the fiber of Ad5, into which a sequence encoding an antibody fragment (of the scFv type) is inserted at the end of one of the 22 repetitive units of the stem with the aim of modifying the specificity of infection towards cells having the target antigen. U.S. Pat. No. 5,543,328 describes an Ad5 chimeric fiber in which the head domain is replaced by tumor necrosis factor (TNF) so as to interact with the cellular receptor for TNF. In another construct, the Ad5 native fiber is fused at its C-terminal end with the peptide ApoE allowing binding to the LDL (for low density lipoprotein) receptor present at the surface of hepatic cells. WO95/26412 describes a fiber modified by incorporation of a ligand at the C-terminal end which conserves its trimerization capacities. WO96/26281 describes a chimeric fiber obtained by replacing part of the native fiber and, in particular, the head, with the equivalent part of an adenoviral fiber of another serotype and, optionally, by inserting at the C-terminal end a peptide RGD which is specific for vitronectin.

As indicated above, the specificity of infection of an adenovirus is determined by the attachment of the adenoviral fiber to a cellular receptor situated at the surface of permissive cells.

French patent application 97 01005 has identified the role of the antigens of the class I major histocompatibility complex and of the III modules of fibronectin as primary receptor and as cofactor, respectively, for adenoviruses. However, other proteins may be involved. In this regard, recent studies have presumed the use of the cellular receptor for the coxsackie viruses by the types 2 and 5 adenoviruses to penetrate into their target cells (Bergelson et al., 1997, Science 275, 1320–1323). The problem which the present invention proposes to solve is to modify the region for interaction of the adenoviral fiber with the cellular receptor (s) in order to alter the natural host specificity of the adenoviruses carrying the mutated fiber. For ease of understanding, the term "cellular receptor" for adenoviruses will be used hereinafter to designate the cellular polypeptide (s) involved directly or otherwise in the binding of adenoviruses to their natural target cells or in the penetration into the latter. Of course, said receptor may be different depending on the serotypes. The addition of a ligand makes it possible to confer a new tropism toward one or more specific cell types carrying at their surface a target molecule recognized by the ligand in question.

The present invention constitutes an improvement of the previous technique since it discloses the regions of the fiber to be mutated in order to inhibit or prevent binding to the natural cellular receptor for adenoviruses. One or more residues of the 443 to 462 region of the head of the Ad5 fiber have now been substituted or deleted and an inhibition of the infectivity of the corresponding adenoviruses toward normally permissive cells has now been shown. The introduction of the GRP (for gastrin releasing peptide) ligand into these fibers should make it possible to target the infection toward cells expressing the GRP receptor. The aim of the present invention is to reduce the therapeutic quantities of adenoviruses to be used and to target the infection at the cells to be treated. This specificity is essential when an adenovirus expressing a cytotoxic gene is used, in order to avoid the propagation of the cytotoxic effect to healthy cells. The advantages offered by the present invention are to reduce the risks of dissemination and the secondary effects linked to the adenoviral technology.

Accordingly, the subject of the present invention is an adenovirus fiber modified by mutation of one or more residues of said fiber, characterized in that said residues are directed toward the natural cellular receptor for said adenovirus.

The term "fiber" is widely defined in the introductory part. The fiber of the present invention may be derived from an adenovirus of human, canine, avian, bovine, murine, ovine, porcine or simian origin or may be a hybrid and may comprise fragments of diverse origins. As regards human adenoviruses, the use of those of serotype C and, in particular, the type 2 or 5 adenoviruses (Ad2 or Ad5) is preferred. It is indicated that the Ad2 fiber contains 580 amino acids (aa) whose sequence is disclosed in Herissé et al. (1981, Nucleic Acid Res. 9, 4023–4042). That of Ad5 has 582 aa and its sequence, presented in the sequence identifier 1 (SEQ ID NO: 1) has been determined by Chroboczek and Jacrot (1987, Virology 161, 549–554). When the fiber of the present invention originates from an animal adenovirus, bovine adenoviruses and, in particular, those of the BAV-3 strain are preferably used. The latter have been the subject of numerous studies and the sequence of the fiber is disclosed in international application WO95/16048. Of course, the fiber of the present invention may exhibit other modifications compared to the native sequence, other than those which are the subject of the present invention.

In accordance with the aims pursued by the present invention, the fiber according to the invention is modified so as to reduce or abolish its capacity to bind to the natural cellular receptor. Such a property may be verified by studying the infectivity or the cellular binding of the corresponding viruses by applying the techniques of the art such as those detailed below. According to an advantageous embodiment, the trimerization and penton-base-binding properties are not affected.

For the purposes of the present invention, the term "mutation" designates a deletion, substitution or addition of one or more residues or a combination of these possibilities. The case where the regions for interaction with the natural cellular receptor are deleted completely or partly and replaced in particular with a ligand specific for a cell surface protein other than the natural receptor for adenoviruses is most particularly preferred.

The three-dimensional crystallographic structure of the adenoviral head has been determined by Xia et al. (1994, Structure 2, 1259–1270). Each monomer contains 8 antiparallel β sheets designated A to D and G to J and 6 major loops of 8 to 55 residues. For example, the CD loop links the β sheet C to the β sheet D. It is indicated that the minor sheets E and F are considered to be part of the DG loop situated between the D and G sheets. As a guide, Table 1 indicates the location of these structures in the amino acid sequence of the fiber of Ad5 as shown in the sequence identifier No. 1 (SEQ ID NO: 1), +1 representing the initiator Met residue. In general, the sheets form an ordered and compact structure whereas the loops are more flexible. These terms are conventional in the field of protein biochemistry and are defined in basic manuals (see for example Stryer, Biochemistry, 2nd edition, Chap 2, p 11 to 39, Ed. Freeman and Company, San Francisco).

TABLE 1

| β sheet | | loop | |
|---|---|---|---|
| nomenclature | residues | nomenclature | residues |
| A | 400 to 403 | AB | 404 to 418 |
| B | 419 to 428 | — | — |
| C | 431 to 440 | CD | 441 to 453 |
| D | 454 to 461 | DG | 462 to 514 |
| G | 515 to 521 | GH | 522 to 528 |
| H | 529 to 536 | HI | 537 to 549 |
| I | 550 to 557 | IJ | 558 to 572 |
| J | 573 to 578 | | |

The four β sheets A, B, C and J constitute the V sheets directed toward the viral particle. The other four (D, G, H and I) form the R sheets, which are supposed to face the cellular receptor. The V sheets appear to play an important role in the trimerization of the structure whereas the R sheets are thought to be involved in the interaction with the receptor. The residues of the fiber of Ad2, Ad3, Ad5, Ad7, Ad40, Ad41 and of the canine adenovirus CAV forming these different structures are clearly indicated in the preceding reference.

The modifications of the adenoviral fiber according to the invention affect more particularly the domain extending from the CD loop to the I sheet and involve in particular residues 441 to 557 of the Ad5 fiber and 441 to 558 of the Ad2 fiber. As a result of their spatial location in the native fiber, these residues are capable of recognizing and/or interacting directly or indirectly with the natural cellular receptor for the adenovirus in question. Inside this region, it is preferable to modify the part which comprises the CD loop, the D sheet and the proximal part of the DG loop (positions 441 to 478 of the Ad2 and Ad5 fiber) and, more particularly, the region extending from residues 443 to 462 as regards Ad5 or 451 to 466 in the case of Ad2. The other target region for the modifications is the H sheet (aa 529 to 536 of the Ad5 fiber and of the Ad2 fiber). Another alternative consists in the modification of the minor sheets E (aa 479–482 Ad5) and F (aa 485–486 Ad5).

As indicated above, it is possible to carry out the procedure by substituting one or more amino acids in the regions exposed. There may be mentioned in this regard the following examples which are derived from the Ad5 fiber in which:
- the glycine residue at position 443 is substituted by an aspartic acid,
- the leucine residue at position 445 is substituted by a phenylalanine,
- the glycine residue at position 450 is substituted by an asparagine,
- the threonine residue at position 451 is substituted by a lysine,
- the valine residue at position 452 is substituted by an asparagine,
- the alanine residue at position 455 is substituted by a phenylalanine,
- the leucine residue at 457 is substituted by an alanine or a lysine, and/or
- the isoleucine residue at position 459 is substituted by an alanine.

It is also possible to introduce several substitutions into the targeted region of the fiber, in particular at the level of the amino acids forming an elbow, preferably of the αα type (see Table 2 by Xia et al., 1994, supra). By way of illustration, there may be mentioned the following two examples in which the Ad5 fiber is modified by substitution:
- of the glycine residue at position 443 by an aspartic acid,
- of the serine residue at position 444 by a lysine, and
- of the alanine residue at position 446 by a threonine; or
- of the serine residue at position 449 by an aspartic acid,
- of the glycine residue at position 450 by a lysine,
- of the threonine residue at position 451 by a leucine, and
- of the valine residue at position 452 by a threonine.

Of course, the replacement amino acids are only mentioned as guide and any amino acid may be suitable for the purposes of the present invention. It is preferable, nevertheless, not to drastically modify the three-dimensional structure. Preferably, the amino acids forming an elbow will be replaced by residues forming a similar structure such as those described in the Xia et al. reference already mentioned.

The fiber of the present invention may also be modified by deletion. The region eliminated may involve all or part of the domain exposed and, in particular, of the CD loop, of the D sheet, of the DG loop and/or of the E and F sheets. As regards an Ad5 fiber according to the invention, there may be mentioned more particular the deletion:
- of the region extending from the serine at position 454 to the phenylalanine at position 461,
- of the region extending from the valine at position 441 to the glutamine at position 453,
- of the region extending from the valine at position 441 to the phenylalanine at position 461, or
- of the region extending from the asparagine at position 479 to the threonine at position 486.

It is also possible to generate other mutants from substitution or deletion in the other sheets or loops, such as for example the G, H and I sheets and the HI and DG loops.

According to an advantageous embodiment, when at least one of the modifications is a deletion of at least 3 consecutive residues of a loop and/or of a sheet, the deleted residues may be replaced by residues of an equivalent loop and/or sheet derived from a fiber of a second adenovirus capable of interacting with a cellular receptor different from that recognized by the first adenovirus. The second adenovirus may be of any origin, human or animal. This makes it possible to maintain the structure of the fiber according to the invention while conferring on it a host specificity corresponding to that of the second adenovirus. As indicated in Xia et al. (1994, supra), the cellular receptor mediating the infection by types 2 and 5 adenoviruses is different from that interacting with the types 3 and 7 adenoviruses. Thus, an Ad5 or Ad2 fiber deleted for at least 3 consecutive residues among those specified above may be substituted by the residues derived from an equivalent region of the Ad3 or Ad7 fiber in order to reduce its capacity to bind the Ad5 receptor and confer on it a new specificity toward the cellular receptor for Ad3 or Ad7. By way of nonlimiting example, there may be mentioned the replacement of the LAPISGTVQSAHLIITRFD (SEQ ID NO: 41) residues (positions 445 to 462) of the Ad5 fiber with the VNTLFKNKNVSINVELYFD (SEQ ID NO: 42) residues of the Ad3 fiber of the replacement of the PVTLTITL (SEQ ID NO: 43) residues (position 529 to 536) of the fiber of Ad5 with the PLEVTVML (SEQ ID NO: 44) residues of the fiber of Ad3.

The present invention also relates to an adenovirus fiber having a substantially reduced capacity for binding to the natural cellular receptor and nevertheless capable of trimerizing and of binding the penton base. As indicated above, the natural cellular receptor is advantageously chosen from the group consisting of the class I major histocompatibility antigens, fibronectin and the cellular receptor for the coxsackie viruses (CAR) or any other cell surface determinant which is usually involved or which participates in the infectivity of adenoviruses.

According to an equally advantageous embodiment, the fiber according to the invention comprises, in addition, a ligand. For the purposes of the present invention, the term ligand defines any entity capable of recognizing and binding, preferably with a high affinity, a cell surface molecule different from the natural cellular receptor. This molecule may be expressed or exposed at the surface of the cell which it is desired to target (cell surface marker, receptor, antigenic peptide presented by histocompatibility antigens and the like). In accordance with the aims pursued by the present invention, a ligand may be an antibody, a peptide, a hormone, a polypeptide or a sugar. The term antibody comprises in particular monoclonal antibodies, antibody fragments (Fab) and single-chain antibodies (scFv). These names and abbreviations are conventional in the field of immunology.

Within the framework of the present invention, it may be advantageous to target more particularly a tumor cell, an infected cell, a particular cell type or a category of cells carrying a specific surface marker. For example, if the host cell to be targeted is a cell infected with the HIV virus (Human Immunodeficiency Virus), the ligand may be a fragment of antibody against fusin, the CD4 receptor or against an exposed viral protein (envelope glycoprotein) or the part of the TAT protein of the HIV virus extending from residues 37 to 72; (Fawell et al., 1994, Proc. Natl. Acad. Sci. USA 91, 664–668). As regards a tumor cell, the choice will be on a ligand recognizing an antigen specific for tumors (for example the MUC-1 protein in the case of breast cancer, some epitopes of the E6 or E7 proteins of the papillomavirus HPV) or overexpressed (receptor for IL-2 overexpressed in some lymphoid tumors, GRP peptide, for Gastrin Releasing Peptide, overexpressed in lung carcinoma cells (Michael et al., 1995 Gene Therapy 2, 660–668) and in pancreas, prostate and stomach tumors). If it is desired to target the T lymphocytes, it is possible to use a ligand for the T cell receptor. Moreover, transferrin is a good candidate for hepatic screening. In general, the ligands which may be used in the context of the invention are widely described in the literature and may be cloned by standard techniques. It is also possible to synthesize them by the chemical route and to couple them to the fiber according to the invention. In this regard, the coupling of galactosyl residues should confer a hepatic specificity because of the interaction with the asialoglycoprotein receptors. However, the preferred embodiment consists in inserting the ligand at the C-terminal end of the fiber according to the invention or as a replacement for the deleted residues when at least one of the modifications is a deletion of at least 3 consecutive residues.

The present invention also relates to a DNA fragment encoding a fiber according to the invention as well as to a vector for expressing such a fragment. Any type of vector may be used to this effect, whether it is of plasmid or viral origin, integrative or otherwise. Such vectors are commercially available or are described in the literature. Likewise, persons skilled in the art are capable of adapting the regulatory elements necessary for the expression of the DNA fragment according to the invention. In addition, it may be combined with one or more substances capable of improving the transfection efficiency and/or the stability of the vector. These substances are widely documented in the literature accessible to persons skilled in the art (see for example Felgner et al., 1989, Proc. West. Pharmacol. Soc. 32, 115–121; Hodgson and Solaiman, 1996, Nature Biotechnology 14, 339–342; Remy et al., 1994, Bioconjugate chemistry 5, 647–654). By way of nonlimiting illustration, these may be polymers, lipids, in particular cationic lipids, liposomes, nuclear proteins and neutral lipids. A combination which can be envisaged is a vector combined with cationic lipids (DC-Chol, DOGS and the like) and neutral lipids (DOPE).

The present invention also relates to an adenovirus lacking a functional native fiber and which comprises, at its surface, a fiber according to the invention. The latter may be expressed by the adenoviral genome or provided in trans by a complementation cell line, such as those defined below. It may, in addition, comprise a ligand as defined above. Preferably, the specificity of binding of such an adenovirus to its natural cellular receptor is significantly reduced or, even better, abolished, because of the modified fiber which it carries. The loss of the natural specificity may be evaluated by studies of cellular attachment carried out in the presence of labeled viruses (for example labeled with $^3$H-thymidine according to the technique of Roelvink et al., 1996, J. Virol. 70, 7614–7621) or by studies of infectivity of cells which are permissive or which express the surface molecule targeted by the ligand (see the examples which follow).

The ligand may be chemically coupled to the adenovirus according to the invention. However, the variant according to which the sequences encoding the ligand are inserted into the adenoviral genome, in particular, into sequences encoding the modified fiber according to the invention, preferably, in phase in order to preserve the reading frame, is preferred. The insertion may take place at any site. However, the preferred site of insertion is upstream of the stop codon at the C-terminal end or in place of the deleted residues. It is also possible to envisage introducing the sequences of the ligand into other adenoviral sequences, in particular those encoding another capsid protein, such as the hexon or the penton.

Advantageously, an adenovirus according to the invention is recombinant and replication-defective, that is to say incapable of autonomously replicating in a host cell. The deficiency is obtained by mutation or deletion of one or more essential viral genes and, in particular, of all or part of the E1 region. Deletions in the E3 region may be envisaged in order to increase the cloning capacities. However, it may be advantageous to conserve the sequences encoding the gp19 k protein (Gooding and Wood, 1990, Critical Reviews of Immunology 10, 53–71) in order to modulate the immune responses of the host. Of course, the genome of an adenovirus according to the invention may also comprise additional deletions or mutations affecting other regions, in particular the E2, E4 and/or L1–L5 regions (see for example international application WO94/28152 and Ensinger et al., 1972, J. Virol. 10, 328–339 describing the heat-sensitive mutation of the DBP gene of E2).

According to a preferred embodiment, an adenovirus according to the invention is recombinant and comprises one or more genes of interest placed under the control of the elements necessary for their expression in a host cell. The gene in question may be of any origin, genomic, cDNA (complementary DNA) or hybrid (minigene lacking one or more introns). It may be obtained by conventional molecular biology techniques or by chemical synthesis. It may encode an antisense RNA, a ribozyme or an mRNA which will then be translated into a polypeptide of interest. The latter may be cytoplasmic, membranal or may be secreted from the host cell. Moreover, it may be all or part of a polypeptide as found in nature, a chimeric polypeptide obtained from the fusion of sequences of diverse origins, or of a polypeptide mutated relative to the native sequence having improved and/or modified biological properties.

In the context of the present invention, it may be advantageous to use the genes encoding the following polypeptides:

cytokines or lymphokines (α-, β- and γ-interferons, interleukins and in particular IL-2, IL-6, IL-10 or IL-12, tumor necrosis factors (TNF), colony stimulating factors (GM-CSF, C-CSF, M-CSF and the like);

cellular or nuclear receptors, in particular those recognized by pathogenic organisms (viruses, bacteria or parasites) and, preferably, by the HIV virus or their ligands (fas ligand);

proteins involved in a genetic disease (factor VII, factor VIII, factor IX, dystrophin or minidystrophin, insulin, CFTR protein (Cystic Fibrosis Transmembrane Conductance Regulator), growth hormones (hGH);

enzymes (urease, renin, thrombin and the like);

enzyme inhibitors (α1-antitrypsin, antithrombin III, viral protease inhibitors and the like);

polypeptides with antitumor effect which are capable of at least partially inhibiting the initiation or the progression of tumors or cancers (antibodies, inhibitors acting on cell division or transduction signals, products of expression of tumor suppressor genes, for example p53 or Rb, proteins stimulating the immune system and the like);

proteins of the class I or II major histocompatibility complex or regulatory proteins acting on the expression of the corresponding genes;

polypeptides capable of inhibiting a viral, bacterial or parasitic infection or its development (antigenic polypeptides having immunogenic properties, antigenic epitopes, antibodies, transdominant variants capable of inhibiting the action of a native protein by competition and the like);

toxins (herpes simplex virus 1 thymidine kinase (HSV-1-TK), ricin, cholera toxin, diphtheria toxin and the like) or immunotoxins, markers (β-galactosidase, luciferase and the like), polypeptide having an effect on apoptosis (inducer of apoptosis: Bax and the like, inducer of apoptosis Bcl2, Bclx), cytostatic agents (p21, p16, Rb and the like), apolipoproteins (apoE and the like), SOD, catalase, nitric oxide synthase (NOS); and growth factors (FGF for Fibroblast growth Factor, VEGF for Vascular Endothelial, cell growth Factor and the like).

It should be noted that this list is not limiting and that other genes may also be used.

Moreover, an adenovirus according to the invention may, in addition, comprise a selectable gene which makes it possible to select or identify the infected cells. There may be mentioned the genes neo (encoding neomycin phosphotransferase) conferring resistance to the antibiotic G418, dhfr (Dihydrofolate Reductase), CAT (Chloramphenicol Acetyl transferase), pac (Puromycin Acetyl-Transferase) or gpt (Xanthine Guanine Phosphoriboxyl Transferase). In general, the selectable genes are known to a person skilled in the art.

Elements necessary for the expression of a gene of interest in a host cell are understood to mean all the elements allowing its transcription into RNA and the translation of an mRNA into a protein. Among these, the promoter is of particular importance. In the context of the present invention, it may be derived from any gene of eukaryotic or even viral origin and may be constitutive or regulatable. Moreover, it may be modified so as to improve the promoter activity, suppress a transcription-inhibiting region, make a constitutive promoter regulatable or vice versa, introduce a restriction site and the like. Alternatively, it may be the natural promoter of the gene to be expressed. There may be mentioned, by way of examples, the CMV (Cytomegalovirus) viral promoter, the RSV (Rous Sarcoma Virus) viral promoter, the promoter of the HSV-1 virus TK gene, the early promoter of the SV40 virus (Simian Virus 40), the adenoviral MLP promoter or the eukaryotic promoters of the murine or human genes for PGK (Phospho Glycerate kinase), MT (metallothionein), $\alpha$1-antitrypsin and albumin (liver-specific), immunoglobulins (lymphocyte-specific). It is also possible to use a tumor-specific promoter ($\alpha$-fetoprotein AFP, Ido et al., 1995, Cancer Res. 55, 3105–3109; MUC-1; PSA for prostate specific antigen, Lee et al., 1996, J. Biol. Chem. 271, 4561–4568; and flt1 specific for endothelial cells, Morishita et al., 1995, J. Biol. Chem. 270, 27948–27953).

Of course, a gene of interest in use in the present invention may, in addition, comprise additional elements necessary for the expression (intron sequence, signal sequence, nuclear localization sequence, transcription terminating sequence, site for initiation of translation of the IRES type and the like) or for its maintenance in the host cell. Such elements are known to persons skilled in the art.

The invention also relates to a method of preparing an adenovirus according to the invention, according to which the genome of said adenovirus is transfected into an appropriate cell line, said transfected cell line is cultured under appropriate conditions in order to allow the production of said adenovirus, and said adenovirus is recovered from the culture of said transfected cell line and, optionally, said adenovirus is substantially purified.

The choice of the cell line depends on the deficient functions in the adenovirus according to the invention and a complementation line capable of providing in trans the deficient function(s) will be used. The 293 line is suitable for complementing the E1 function (Graham et al., 1977, J. Gen. Virol. 36, 59–72). For a double deficiency E1 and E2 or E4, it is possible to use a line among those described in French patent application 96 04413. It is also possible to use a helper virus to complement the defective adenovirus according to the invention in any host cell or a mixed system using complementation cell and helper virus in which the elements are dependent on each other. The means for propagating a defective adenovirus are known to a person skilled in the art who may refer, for example, to Graham and Prevec (1991, Methods in Molecular Biology, vol. 7, p. 190–128; Ed. E. J. Murey, The Human Press Inc.). The adenoviral genome is preferably reconstituted in vitro in *Escherichia coli* (*E. coli*) by ligation or by homologous recombination (see for example French application 94 14470). The methods of purification are described in the state of the art. There may be mentioned the density gradient centrifugation technique.

The present invention also relates to a cell line comprising, either in a form integrated into the genome or in the form of an episome, a DNA fragment encoding a fiber according to the invention, placed under the control of the elements allowing its expression. Said line may, in addition, be capable of complementing an adenovirus deficient for one or more functions selected from those encoded by the E1, E2, E4 and L1–L5 regions. It is preferably derived from the 293 line. Such a line may be useful for the preparation of an adenovirus whose genome lacks all or part of the sequences encoding the fiber (so as to produce a nonfunctional fiber). The subject of the present invention is also the corresponding method, according to which:

the genome of said adenovirus is transfected into a cell line according to the invention, said transfected cell line is cultured under appropriate conditions in order to allow the production of said adenovirus, and said adenovirus is recovered from the culture of said transfected cell line and, optionally, said adenovirus is substantially purified.

The present invention also covers a host cell infected with an adenovirus according to the invention or capable of being obtained by a method according to the invention. This is advantageously a mammalian cell and, in particular, a human cell. It may be a primary or tumor cell and of any origin, for example of hematopoietic origin (totipotent stem cell, leukocyte, lymphocyte, monocyte or macrophage and the like), muscle (satellite cell, myocyte, myoblast, smooth muscle cell), cardiac, nasal, pulmonary, tracheal, hepatic, epithelial or fibroblast origin.

The subject of the invention is also a pharmaceutical composition comprising, as therapeutic or prophylactic agent, a host cell or an adenovirus according to the invention or capable of being obtained by a method according to the invention, in combination with a pharmaceutically acceptable carrier. The composition according to the invention is, in particular, intended for the preventive or curative treatment of diseases such as genetic diseases (hemophilia, cystic fibrosis, diabetes, Duchenne's. myopathy or Becker's myopathy and the like), cancers, such as those induced by oncogenes or viruses, viral diseases, such as hepatitis B or C and AIDS (acquired immunodeficiency syndrome resulting from HIV infection), recurring viral diseases, such as viral infections caused by the herpesvirus and cardiovascular diseases including restenoses.

A pharmaceutical composition according to the invention may be manufactured conventionally. In particular, a therapeutically effective quantity of the therapeutic or prophylactic agent is combined with a carrier such as a diluent. A composition according to the invention may be administered by the local, systemic or aerosol route, in particular by the intragastric, subcutaneous, intracardiac, intra-muscular, intravenous, intraperitoneal, intratumor, intrapulmonary, intranasal or intracheal route. The administration may take place in a single dose or repeated once or several times after a certain time interval. The appropriate route of administration and the appropriate dosage vary according to various parameters, for example, the individual or patient to be treated or the gene(s) of interest to be transferred. In particular, the viral particles according to the invention may be formulated in the form of doses of between $10^4$ and $10^{14}$ pfu (plaque-forming units), advantageously $10^5$ and $10^{13}$ pfu and, preferably, $10^6$ and $10^{12}$ pfu. The formulation may also include a diluent, an adjuvant, a pharmaceutically acceptable excipient as well as a stabilizer, preservative and/or solubilizer. A formulation in saline, nonaqueous or isotonic solution is particularly suitable for an injectable administration. It may be provided in liquid or dry form (for example a lyophilisate and the like) or any other galenic form commonly used in the pharmaceutical field.

Finally, the present invention relates to the therapeutic or prophylactic use of an adenovirus or of a host cell according to the invention or of an adenovirus capable of being obtained by a method according to the invention, for the preparation of a medicament intended for the treatment of the human or animal body by gene therapy. According to a first possibility, the medicament may be administered directly in vivo (for example by intravenous injection, into an accessible tumor, into the lungs by aerosol and the like). It is also possible to adopt the ex vivo approach which consists in collecting cells from the patient (bone marrow stem cells, peripheral blood lymphocytes, muscle cells and the like), transfecting or infecting them in vitro according to prior art techniques and readministering them to the patient.

The invention also extends to a method of treatment according to which a therapeutically effective quantity of an adenovirus or of a host cell according to the invention is administered to a patient requiring such a treatment.

EXAMPLES

The following examples illustrate only an embodiment of the present invention.

The constructs described below are prepared according to general genetic engineering and molecular cloning techniques detailed in Maniatis et al., (1989, Laboratory Manual, Cold Spring Harbor, Laboratory Press, Cold Spring Harbor, N.Y.) or according to the manufacturer's recommendations when a commercial kit is used. The cloning steps using bacterial plasmids are preferably carried out in the E. coli 5K (Hubacek and Glover, 1970, J. Mol. Biol. 50, 111–127) or BJ 5183 (Hanahan, 1983, J. Mol. Biol. 166, 557–580) strain. This latter strain is preferably used for the homologous recombination steps. The strain NM522 (Strategene) is suitable for the propagation of the M13 phage vectors. The PCR amplification techniques are known to persons skilled in the art (see for example PCR Protocols-A guide to methods and application, 1990, edited by Innis, Gelfand, Sninsky and White, Academic Press Inc). As regards the repair of the restriction sites, the technique used consists in filling the protruding 5' ends with the aid of the large fragment of E. coli DNA polymerase I (Klenow). The Ad5 nucleotide sequences are those used in the Genebank data bank under the reference M73260.

As regards the cell biology, the cells are transfected according to standard techniques well known to persons skilled in the art. There may be mentioned the calcium phosphate technique (Maniatis et al., supra), but any other protocol may also be used, such as the DEAE dextran technique, electroporation, methods based on osmotic shocks, microinjection or methods based on the use of cationic lipids. As for the culture conditions, they are conventional. In the examples which follow, the human line 293 (ATCC CRL1573) and the murine lines Swiss 3T3 (ATCC CCL92), NR6 (Wells et al., 1990, Science 247: 962–964), NR6-hEGFR (Schneider et al., 1986, Proc. Natl. Acad. Sci. USA 83, 333–336), Daudi HLA– (ATCC CCL213) and Daudi HLA+ (Quillet et al., 1988, J. Immunol. 141, 17–20) are used. It is indicated that the Daudi line is established from a Burkitt lymphoma and is naturally deficient in the expression of β2-microglobulin and, as a result, does not possess the class I HLA molecules at its surface (Daudi HLA–). The Daudi-derived cell line E8.1 was generated by transfection of a gene encoding β2-microglobulin in order to restore the expression of class I HLA molecules at their surface (Daudi-HLA+; Quillet et al., 1988, J. Immunol. 141, 17–20). It is understood that other cell lines may also be used.

Example 1

Construction of an Adenovirus Exhibiting a Host Tropism Toward the Cells Expressing the GRP (for gastrin releasing peptide) Receptor A. Insertion of the Sequences Encoding the GRP Ligand (GRP fiber).

The plasmid pTG6593 is derived from p poly II (Lathe et al., 1987, Gene 57, 193–201) by introducing the complete gene encoding the Ad5 fiber in the form of an EcoRI-SmaI fragment (nucleotides (nt) 30049 to 33093). The HindIII-SmaI fragment (nt 31994–33093) is isolated and cloned into M13TG130 (Kieny et al., 1983, Gene 26, 91–99) digested with these same enzymes, in order to give M13TG6526. The latter is subjected to site-directed mutagenesis with the aid of the oligonucleotide oTG7000 (SEQ ID NO: 2) (Sculptor kit, in vitro mutagenesis, Amersham) in order to introduce an adaptor encoding a spacer arm of 12 amino acids having the sequence PSASASASAPGS (SEQ ID NO: 45). The mutated vector thus obtained, M13TG6527, is subjected to a second mutagenesis which makes it possible to introduce the sequence encoding the 10 residues of the GRP peptide (GNHWAVGHLM (SEQ ID NO: 46); Michael et al., 1995, Gene Ther. 2, 660–668). The oligonucleotide oTG7001 (SEQ ID NO: 3) is used to this effect. The HindIII-SmaI fragment is isolated from the mutated phage M13TG6528 and introduced by the homologous recombination technique (Chartier et al., 1996, J. Virol. 70, 4805–4810) into the plasmid pTG6590 carrying the Ad5 adenoviral genome fragment extending from nt 27081 to 35935 and linearized with MunI (nt 32825). The SpeI-ScaI fragment (carrying nt 27082 to 35935 of the Ad5 genome which are modified by introduction of the spacer arm and of the GRP peptide) is isolated from the preceding vector designated pTG8599 and then exchanged for the equivalent fragment of pTG6591 previously digested with these same enzymes. As a guide, pTG6591 comprises the wild-type adenoviral sequences from positions 21562 to 35935. pTG4600 is obtained from which the BstEII fragment (nt 24843 to 35233) is isolated. After homologous recombination with the plasmid pTG3602 which comprises the Ad5 genome (described in greater detail in international application WO96/17070), the vector pTG4601 is generated.

A cassette allowing the expression of the LacZ gene is introduced in place of the E1 adenoviral region by homologous recombination between the plasmid pTG4601 linearized with ClaI and a fragment BsrGI-PstI comprising the LacZ gene encoding β-galactosidase under the control of the Ad2 MLP promoter and the SV40 virus polyadenylation signal. This fragment is isolated from the vector pTG8526 containing the 5' end of the viral genomic DNA (nt 1 to 6241) in which the E1 region (nt 459 to 3328) is replaced with the LacZ expression cassette. Its construction is within the capability of persons skilled in the art. The final vector is designated pTG4628.

The corresponding viruses AdTG4601 and AdTG4628 are obtained by transfection of the adenoviral fragments liberated from the plasmid sequences by PacI digestion into the 293 line. As a guide, AdTG4601 carries the complete Ad5 genome in which the gene for the fiber comprises at its 3' end a spacer arm followed by the GRP peptide. The recombinant virus AdTG4628 carries, in addition, the cassette for expression of the LacZ reporter gene under the control of the MLP adenoviral promoter.

B. Study of the Tropism of the Virus Carrying the GRP Fiber.

The presence of the GRP peptide in the adenoviral fiber makes it possible to target the cells expressing at their surface the GRP receptor. The expression of the messengers encoding the latter is studied in the 293 cells and in the murine Swiss-3T3 cells (Zachary et al., 1985, Proc. Natl. Acad. Sci. USA. 82, 7616–7620) by Northern blotting. There is used, as probe, a mixture of 2 DNA fragments complementary to the sequence encoding the GRP receptor which are labeled by conventional techniques with the $^{32}$P isotope. As a guide, the fragments are produced by reverse PCR from total cell RNAs with the aid of the oligonucleotides oTG10776 (SEQ ID NO: 4) and oTG10781 (SEQ ID NO: 5) (Battey et al., 1991, Proc. Natl. Acad. Sci. USA 88, 395–399; Corjay et al., 1991, J. Biol. Chem. 266, 18771–18779). The intensity of the mRNAs detected is much higher in the case of the Swiss-3T3 cells than in the 293 cells, indicating the overexpression of the GRP receptor by the murine line.

Competition experiments are carried out on the 2 types of cells. The competitor consists of the head of the Ad5 fiber produced in E. coli whose adenoviral cellular-receptor binding properties have been shown (Henry et al., 1994, J. Virol 68, 5239–5246). The monolayer cells are previously incubated for 30 minutes in the presence of PBS or of increasing concentrations of recombinant Ad5 head (0.1 to 100 μg/ml) in DMEM medium (Gibco BRL) supplemented with 2% fetal calf serum (FCS). Next, the virus AdTG4628 whose fiber contains the GRP peptide is added at a multiplicity of infection of 0.001 infectious unit/cell for 24 h at 37° C. The recombinant virus AdLacZ (Stratford-Perricaudet et al., 1992, J. Clin. Invest. 90, 626–630) which carries a native gene for the fiber, is used as control and based on the same experimental conditions. The cells are then fixed and the expression of the LacZ gene evaluated (Sanes et al., 1986, EMBO J. 5, 3133–3142). The number of blue cells is representative of the efficiency of the viral infection. An inhibition by competition results in a reduction in the number of colored cells compared with a control without competitor (PBS).

The addition of recombinant Ad5 head at a concentration of 100 μg/ml strongly inhibits the infection of the 293 cells by the AdLacZ and AdTG4628 viruses (inhibition level of 95 and 98%). This suggests that the presence of the competitor prevents the interaction of the adenoviral fiber with its natural cellular receptor. On the other hand, the two viruses have a different behavior on the Swiss-3T3 cells. The infection of the AdTG4628 virus in the presence of 100 μg/ml of competitor is only partially inhibited whereas, under the same experimental conditions, that of the AdLacZ virus having the native fiber is completely inhibited. These results suggest that the infection of the Swiss-3T3 cells with AdTG4628 is partly mediated by an independent receptor, probably the GRP receptor which these cells overexpress. In conclusion, the addition of the GRP ligand to the C-terminal end of the fiber promotes the infection of the cells expressing the GRP receptor independently of the fiber-natural cellular receptor interaction.

Example 2

Construction of an Adenovirus Exhibiting a Host Tropism Toward the Cells Expressing the EGF (Epidermal Growth Factor) Receptor This example describes a fiber carrying the EGF sequences at its C-terminal end. For that, the oligonucleotides oTG11065 (SEQ ID NO: 6) and oTG11066 (SEQ ID NO: 7) are used to amplify an HindIII-XbaI fragment from the plasmid M13TG6527. The oligonucleotides oTG11067 (SEQ ID NO: 8) and oTG11068 (SEQ ID NO: 9) make it possible to generate an XhoI-SmaI fragment (going from the stop codon up to nt 33093) from M13TG6527. The DNA complementary to EGF, obtained from ATCC (#59957), is amplified in the form of an XhoI-XbaI fragment with the aid of the oligonucleotides oTG11069 (SEQ ID NO: 10) and oTG11070 (SEQ ID NO: 11). The 3 fragments digested with the appropriate enzymes are then religated in order to give an HindIII-SmaI fragment containing the EGF fused to the C-terminal end of the fiber. The same homologous recombination procedure as that described in Example 1 is applied in order to replace this fragment in its genomic context.

However, it is possible to simplify the cloning steps by introducing a unique BstBI site into the targeted region by conventional mutagenesis techniques. pTG46009 and pTG4213 are obtained with LacZ. The homologous recombination between pTG4609 linearized with BstBI and the preceding HindIII-SmaI fragment generates the plasmid pTG4225 carrying the wild-type E1 region. Its equivalent carrying the LacZ expression cassette pTG4226 is obtained by homologous recombination with pTG4213 digested with BstBI. The viruses AdTG4225 and AdTG4226 may be produced conventionally by transfection of an appropriate cell line for example overexpressing the EGF receptor.

To test the specificity of infection by these viruses, it is possible to use the NR6 murine fibroblast cells and the NR6-hEGFR cells expressing the human EGF receptor. Competitions with the recombinant Ad5 head or with EGF make it possible to evaluate the involvement of the natural cellular receptors and EGF for mediating infection by the viruses.

Example 3

Modifications of the Head of the Fiber in Order to Eliminate the Binding to the Natural Cellular Receptor The mutation of the region of the adenoviral fiber involved in the interaction with the natural cellular receptor was undertaken in order to eliminate the capacity of the fiber to bind its natural receptor and the addition of a ligand will make it possible to modify the tropism of the corresponding adenoviruses.

The sequences of the Ad5 fiber encoding the region extending from residues 443 to 462 and 529 to 536 were subjected to various mutations. The deletion of the D sheet uses the mutagenesis oligonucleotide oTG7414 (SEQ ID NO: 12) and the deletion of the CD loop the oligonucleotide oTGA (SEQ ID NO: 13). The oligonucleotide oTGB (SEQ ID NO: 14) allows, for its part, the deletion of the CD loop and of the D sheet. The oligonucleotide OTG 7416 (SEQ ID NO: 38) allows the deletion of the H sheet. All these oligonucleotides contain a BamHI site which makes it possible to easily detect the mutants and, also, to insert the sequences encoding a ligand, for example the EGF peptide.

Another series of modifications consists in replacing these deleted regions with the equivalent sequences derived from the Ad3 fiber (D+CD5 to D+CD3 means that the CD and D region of the Ad5 fiber is replaced by its equivalent from Ad3). Indeed, many data show that Ad5 and Ad3 do not bind to the same receptor, so that such a substitution should abolish the infection mediated by the Ad5 receptor and target the cells carrying the Ad3 receptor. The replacement of the Ad5 CD loop with that of Ad3 uses oTG11135 (SEQ ID NO: 15), the replacement of the D sheet of the Ad5 fiber with that of the Ad3 fiber is carried out by the oligonucleotide oTG10350 (SEQ ID NO: 16) and the replacement of the D sheet and of the CD loop of Ad5 with those of Ad3 is carried out on the preceding mutant with the aid of oTG11136 (SEQ ID NO: 17). The replacement of the H sheet is carried out with the aid of the oligonucleotide oTG10352 (SEQ ID NO: 39).

This target region of the adenoviral head was also modified by a series of point mutations:

replacement from the αα GSLA elbow to the αα DKLT elbow: oTGC (SEQ ID NO: 18), replacement from the αα SGTV elbow to the αα DKLT elbow: oTGD (SEQ ID NO: 19), G443 to D (G443D): oTGE (SEQ ID NO: 20), L445 to F (L445F) oTGF (SEQ ID NO: 21), G450 to N (G450N): oTGG (SEQ ID NO: 22), T451 to K (T451K): oTGH (SEQ ID NO: 23), V452 to N (V425N): oTGI (SEQ ID NO: 24), A 455 to F (A455F): oTGJ (SEQ ID NO: 25), L457 to K (L457K): oTGK (SEQ ID NO: 26), I459 to A (I459A): oTGL (SEQ ID NO: 27).

The oTGEs to I introduce mutations in the CD loop of the adenoviral fiber on amino acids which are nonconservative between Ad5 and Ad3 whereas the oTGJs to K relate to amino acids of the D sheet which are not engaged in a hydrogen bond stabilizing the structure.

The mutageneses may be carried out on the vector M13TG6526 or M13TG6528. The first carries the wild-type HindIII-SmaI fragment and the second this same fragment modified by insertion of the GRP sequences. The plasmids carrying the adenoviral genome may be reconstituted as described above for the plasmids pTG4609 (wild-type E1) and pTG4213 (LacZ in place of the E1 region). The viruses are generated by transfection of the 293 cells or of cells overexpressing the receptor binding the relevant ligand. Such cells may be generated by transfection of the corresponding complementary DNA. Cells are preferably used which do not naturally express the natural cellular receptor for adenoviruses, for example the Daudi line (ATCC CCL213).

The viability of the various mutants is evaluated by transfection of cells 293 and 293-Fb+ (293 cells transfected with a vector for expressing the wild-type Ad5 fiber). However, the transfection efficiency is variable from one experiment to another, even as regards an adenovirus carrying a wild-type fiber having incorporated the GRP peptide at its C-terminal end (AdFbGRP). To standardize the results, the plaques obtained after transfection of the 293-Fb+ cells are first of all amplified on this same line and the viruses generated are titrated: at this stage, they carry either the wild-type fiber or the mutant fiber or both types. The 293 cells are then infected with these viruses at a low multiplicity of infection which makes it possible to infect only about 10% of the cells (MOI of about 0.2 infectious unit/cell) and the extent of the viral infection is determined at 7 days post-infection by measuring the accumulation of the viral DNA and the viral titer. The propagation of the infection being dependent on the mutated fiber, the advantageous mutants are those which do not give rise to a productive infection, showing that the mutation alters the binding to the natural receptor. The propagation capacity of the adenoviruses carrying the mutated fiber is compared with that of a wild-type adenovirus and of an AdFbGRP.

The results show that the insertion of the GRP peptide at the end of the wild-type fiber slightly reduces the growth of the corresponding virus compared with a wild-type Ad, but the multiplication factor is nevertheless of the order of 1000. The mutations V452N, D+CD5 to D+CD3 and L445F significantly reduce (factor of 3 to 11) the affinity of the mutated fiber head for the natural cellular receptor for adenoviruses. The mutations ΔD (deletion of the D sheet of the Ad5 fiber), ΔCD+D (deletion of the CD loop and of the D sheet), CD5 to CD3 (replacement of the CD loop of an Ad5 with its equivalent from an Ad3), G443D, A455F, L457K and I459A abolish the propagation of the corresponding viruses in the 293 cells (multiplication factor less than 1).

Next, the capacity of the mutant viruses to penetrate into the target cells by means of the GRP receptor is verified. The advantageous mutants are those which exhibit a significant multiplication factor (greater than 1). In this regard, it is possible to use a line designated 293-GRPR expressing MHC-I and the GRP receptor at high levels. It is generated by transfecting the 293 cells with a eukaryotic expression plasmid carrying the cDNA for the GRP receptor (Corjay et al., 1991, J. Biol. Chem. 266, 18771–18779). The expression cassette consists of the early CMV promoter (Boshart et al., 1985, Cell 41, 521), the sequences for splicing the β-globin gene, the cDNA encoding the GRP receptor and the polyA sequences of the β-globin gene. The selection of the transformants is carried out in the presence of hygromycin (350 µg/ml) and 50 clones are selected, amplified and tested for the expression of the mRNA encoding the receptor by the Northern technique. The most productive clones are assembled and designated 293-GRPR. The expression of the protein may also be checked by FACS with the aid of a GRP peptide conjugated with biotin and avidin-FITC followed by detection with the aid of fluoroscein.

Example 4

Insertion of the Ligand into a Capsid Protein Other Than the Fiber in Combination with one of the Abovementioned Modifications of the Fiber This example describes the insertion of the EGF ligand into the hexon capsid protein. Of course, it is preferable for the corresponding adenovirus to have lost its capacity for attachment to the natural cellular receptor. Its genome may for example include a modified fiber gene (see Example 3) or may lack at least part of the sequences of the fiber.

A transfer plasmid is constructed for the homologous recombination covering the region of the Ad5 genome encoding the hexon (nt 18842–21700). The Ad5 HindIII-XhoI fragment (nt 18836–24816) is cloned into pBSK+ (Strategene) digested with these same enzymes in order to give the plasmid pTG4224. The sequences encoding the EGF peptide are introduced into the hypervariable L1 loop of the hexon by creating chimeric fragments by PCR: hexon (nt19043–19647)-XbaI-EGF-BsrGI-hexon (nt19699–20312). The nt19043 to 19647 fragment is obtained by PCR amplification from the plasmid pTG3602 with the oligonucleotides oTG11102 (SEQ ID NO: 28) and oTG11103 (SEQ ID NO: 29). The nt19699 to 20312 fragment is amplified from the same DNA with the oligonucleotides oTG11104 (SEQ ID NO: 30) and oTG11105 (SEQ ID NO: 31). The EGF is cloned from the cDNA with the aid of the oligonucleotides oTG11106 (SEQ ID NO: 32) and oTG11107 (SEQ ID NO: 33) making it possible to place the coding sequence of the EGF in phase with the hexon. The PCR products are digested with the appropriate enzymes and then religated. The chimeric fragment may then be inserted by homologous recombination into the plasmid pTG4224 linearized with NdeI (nt 19549), to give pTG4229. The sequences encoding the modified hexon may be obtained by HindIII-XhoI digestion and replaced in their genomic context by homologous recombination. The vector pTG3602, pTG4607, pTG4629 linearized with SgfI or a vector carrying the adenoviral genome deleted for the fiber sequences (such as pTG4607 described below) or expressing a modified fiber in accordance with Example 3 may be used.

The adenoviral genome incapable of producing a functional native fiber is obtained by a deletion affecting the initiator codon but not extending to the other adenoviral ORFs. The procedure is carried out in the following manner: the adenoviral fragment in 5' of the deletion (nt 30564 to 31041) is amplified by PCR with the aid of the primers oTG7171 and oTG7275 (SEQ ID NO: 34 and 35). The amplification of the fragment in 3' (nt 31129 to 33099) uses the primers oTG7276 and oTG7049 (SEQ ID NO: 36 and 37). The PCR fragments are digested with XhoI and ligated before being introduced by homologous recombination into the vector pTG6591 linearized with NdeI, to give pTG4602. Next, the BstEII fragment isolated from the latter is subjected to a homologous recombination with the vector pTG3602 digested with SpeI. pTG4607 is obtained. The vector pTG4629 is equivalent to pTG4607, but carries, in addition, the LacZ expression cassette in place of E1.

The corresponding viruses may be obtained after transfection of 293 or 293-Fb+ cells or of cells overexpressing the EGF receptor. The study of the specificity of infection may be carried out as previously described using EGF as competitor.

Example 5

Construction of a Mutant of the Fiber Deleted for the E and F Sheets

A deletion mutant for the EF sheets of the domain of the head of the Ad5 fiber was also generated. The plasmid pTG6593 is digested with HindIII and SmaI and the fragment carrying the fiber sequences is isolated and cloned into the vector M13TG130 cleaved with HindIII and SmaI. The deleterious mutation uses the oligonucleotide indicated in SEQ ID NO: 40. The mutated HindIII-SmaI fragment is recombined in *E. coli* with pTG4609 linearized with BstBI (Chartier et al., 1996, J. Virol. 70, 4805–4810). The latter contains the complete Ad5 genome containing a BstBI site at position 32940 downstream of the stop codon of the fiber.

The trimerizing capacity of the modified fiber is tested on NDS-PAGE gel (Novelli and Boulanger, J. of Biological Chemistry, 1991, 266, 9299–9303) using the protein produced by the recombinant route in the insect cells Sf9 with the aid of a recombinant baculovirus carrying the corresponding sequences placed under the control of the polyhedrin promoter. In parallel, the viability (or propagating capacity) of the virions carrying the mutated fiber is determined by transfection of the 293 and 293Fb+ cells. Finally, the binding of the fiber to the MHC-I and CAR cellular receptors may be studied in competition experiments for infection by a recombinant adenovirus Ad5-Luc on Daudi-HLA+ and CHO-CAR cells (Bergelson et al., 1997, Science 275, 1320–1323). As a guide, the virus Ad5Luc is a replication-competent adenovirus which contains the luciferase gene placed under the control of the SV40 virus (Simian Virus 40) early promoter inserted into the E3 region of the adenoviral genome (Mittal et al., 1993, Virus Research 28, 67–90).

The ΔEF fiber accumulates in the form of trimers, can be propagated in 293 and 393Fb+ cells and is not a competitor for the infection of Daudi-HLA+ cells with Ad5Luc. It is capable of partially inhibiting the infection of the CHO-CAR cells, but less efficiently than the wild-type fiber. This assumes that the E and F sheets are important for the attachment of Ad5 to the MHC-1 receptor whereas it plays a more minor role, perhaps of stabilization in the binding to CAR. The insertion of a new ligand should make it possible to redirect the infectivity toward the cells carrying the receptor recognized by the ligand.

What is claimed is:

1. A method for producing an adenovirus whose genome lacks all or part of the sequences encoding a fiber, comprising:

transfecting the genome of said adenovirus into a cell line comprising, either in a form integrated into the genome or in the form of an episome, a DNA fragment or expression vector encoding an adenovirus fiber modified by substitution mutation of one or more residues of a native fiber, wherein said native fiber residues are directed toward the natural cellular receptor recognized by the native adenovirus fiber, and wherein said residues are between the CD loop and the β sheet I of said fiber, the modification not including deletion of the entire knob region, said DNA fragment or expression vector placed under the control of the elements allowing its expression in said cell line, culturing said transfected cell line under appropriate conditions in order to allow the production of said adenovirus, and recovering said adenovirus from the culture of said transfected cell line.

2. The method of claim 1, further comprising substantially purifying said recovered adenovirus.

3. An adenovirus made by the process comprising:

a) identifying one or more residues of a natural adenoviral fiber which are directed toward the natural cellular receptor of a natural adenovirus and which are between the CD loop and the β sheet I of the adenoviral fiber, b) modifying said fiber by mutating one or more of said residues so as to eliminate binding to the natural cellular receptor, but not by deleting the entire knob region, c) either incorporating sequence encoding the modified fiber of step b) into a genome of an adenovirus which lacks a functional native fiber, or providing the modified fiber in trans in a cell line, d) transfecting the genome of said adenovirus into an appropriate cell line, e) culturing said transfected cell line under appropriate conditions in order to allow the production of said adenovirus, and f) recovering said adenovirus from said culture of said transfected cell line.

4. An adenovirus comprising an adenovirus fiber, modified by substitution mutation of one or more residues of a native fiber, wherein said native fiber residues are directed toward the natural cellular receptor recognized by the native adenovirus fiber, and wherein said residues are between the CD loop and the β sheet I of said fiber and further comprising a ligand inserted at the C-terminal end of the fiber, which is capable of recognizing a cell surface molecule different from the natural cellular receptor of said adenovirus in its natural form.

5. The adenovirus of claim 4, wherein said adenovirus is a replication-defective recombinant adenovirus.

6. The adenovirus of claim 5, wherein said adenovirus is deleted for all or part of the E1 region.

7. The adenovirus of claim 6, wherein said adenovirus is further deleted for all or part of the E2, E4 and/or L1–L5 region.

8. The adenovirus of claim 5, wherein said adenovirus comprises a gene of interest selected from the genes encoding a cytokine, a cellular or nuclear receptor, a ligand, a coagulation factor, the CFTR protein, insulin, dystrophin, a growth hormone, an enzyme, and enzyme inhibitor, a polypeptide with antitumor effect, a polypeptide capable of inhibiting a bacterial infection, a polypeptide capable of inhibiting a parasitic infection, a polypeptide capable of inhibiting a viral infection, a polypeptide capable of inhibiting HIV, an antibody, a toxin, an immunotoxin and a marker.

9. The adenovirus of claim 5, wherein said adenovirus is deleted for all or part of the E3 region.

10. The adenovirus of claim 4, wherein the ligand is a polypeptide.

* * * * *

SEQUENCE LISTING

<160> NUMBER OF SEQ ID NOS: 46

<210> SEQ ID NO 1
<211> LENGTH: 581
<212> TYPE: PRT
<213> ORGANISM: Ad5 fiber Mastadenovirus

<400> SEQUENCE: 1

Met Lys Arg Ala Arg Pro Ser Glu Asp Thr Phe Asn Pro Val Tyr Pro
 1               5                  10                  15

Tyr Asp Thr Glu Thr Gly Pro Pro Thr Val Pro Phe Leu Thr Pro Pro
            20                  25                  30

-continued

```
Phe Val Ser Pro Asn Gly Phe Gln Glu Ser Pro Pro Gly Val Leu Ser
         35                  40                  45
Leu Arg Leu Ser Glu Pro Leu Val Thr Ser Asn Gly Met Leu Ala Leu
 50                  55                  60
Lys Met Gly Asn Gly Leu Ser Leu Asp Glu Ala Gly Asn Leu Thr Ser
 65                  70                  75                  80
Gln Asn Val Thr Thr Val Ser Pro Pro Leu Lys Lys Thr Lys Ser Asn
                 85                  90                  95
Ile Asn Leu Glu Ile Ser Ala Pro Leu Thr Val Thr Ser Glu Ala Leu
                100                 105                 110
Thr Val Ala Ala Ala Ala Pro Leu Met Val Ala Gly Asn Thr Leu Thr
             115                 120                 125
Met Gln Ser Gln Ala Pro Leu Thr Val His Asp Ser Lys Leu Ser Ile
 130                 135                 140
Ala Thr Gln Gly Pro Leu Thr Val Ser Glu Gly Lys Leu Ala Leu Gln
 145                 150                 155                 160
Thr Ser Gly Pro Leu Thr Thr Thr Asp Ser Ser Thr Leu Thr Ile Thr
                165                 170                 175
Ala Ser Pro Pro Leu Thr Thr Ala Thr Gly Ser Leu Gly Ile Asp Leu
             180                 185                 190
Lys Glu Pro Ile Tyr Thr Gln Asn Gly Lys Leu Gly Leu Lys Tyr Gly
             195                 200                 205
Ala Pro Leu His Val Thr Asp Asp Leu Asn Thr Leu Thr Val Ala Thr
             210                 215                 220
Gly Pro Gly Val Thr Ile Asn Asn Thr Ser Leu Gln Thr Lys Val Thr
 225                 230                 235                 240
Gly Ala Leu Gly Phe Asp Ser Gln Gly Asn Met Gln Leu Asn Val Ala
                 245                 250                 255
Gly Gly Leu Arg Ile Asp Ser Gln Asn Arg Arg Leu Ile Leu Asp Val
             260                 265                 270
Ser Tyr Pro Phe Asp Ala Gln Asn Gln Leu Asn Leu Arg Leu Gly Gln
             275                 280                 285
Gly Pro Leu Phe Ile Asn Ser Ala His Asn Leu Asp Ile Asn Tyr Asn
 290                 295                 300
Lys Gly Leu Tyr Leu Phe Thr Ala Ser Asn Asn Ser Lys Lys Leu Glu
 305                 310                 315                 320
Val Asn Leu Ser Thr Ala Lys Gly Leu Met Phe Asp Ala Thr Ala Ile
                 325                 330                 335
Ala Ile Asn Ala Gly Asp Gly Leu Glu Phe Gly Ser Pro Asn Ala Pro
             340                 345                 350
Asn Thr Asn Pro Leu Lys Thr Lys Ile Gly His Gly Leu Glu Phe Asp
             355                 360                 365
Ser Asn Lys Ala Met Val Pro Lys Leu Gly Thr Gly Leu Ser Phe Asp
 370                 375                 380
Ser Thr Gly Ala Ile Thr Val Gly Asn Lys Asn Asn Asp Lys Leu Thr
 385                 390                 395                 400
Leu Trp Thr Thr Pro Ala Pro Ser Pro Asn Cys Arg Leu Asn Ala Glu
                 405                 410                 415
Lys Asp Ala Lys Leu Thr Leu Val Leu Thr Lys Cys Gly Ser Gln Ile
             420                 425                 430
Leu Ala Thr Val Ser Val Leu Ala Val Lys Gly Ser Leu Ala Pro Ile
             435                 440                 445
```

```
Ser Gly Thr Val Gln Ser Ala His Leu Ile Ile Arg Phe Asp Glu Asn
    450                 455                 460

Gly Val Leu Leu Asn Asn Ser Phe Leu Asp Pro Glu Tyr Trp Asn Phe
465                 470                 475                 480

Arg Asn Gly Asp Leu Thr Glu Gly Thr Ala Tyr Thr Asn Ala Val Gly
                    485                 490                 495

Phe Met Pro Asn Leu Ser Ala Tyr Pro Lys Ser His Gly Lys Thr Ala
                500                 505                 510

Lys Ser Asn Ile Val Ser Gln Val Tyr Leu Asn Gly Asp Lys Thr Lys
                515                 520                 525

Pro Val Thr Leu Thr Ile Thr Leu Asn Gly Thr Gln Glu Thr Gly Asp
    530                 535                 540

Thr Thr Pro Ser Ala Tyr Ser Met Ser Phe Ser Trp Asp Trp Ser Gly
545                 550                 555                 560

His Asn Tyr Ile Asn Glu Ile Phe Ala Thr Ser Ser Tyr Thr Phe Ser
                565                 570                 575

Tyr Ile Ala Gln Glu
            580

<210> SEQ ID NO 2
<211> LENGTH: 60
<212> TYPE: DNA
<213> ORGANISM: Artificial sequence
<220> FEATURE:
<223> OTHER INFORMATION: Synthetic oligonucleotide OTG7000 (codes for
      PSASASASAPGS)

<400> SEQUENCE: 2
aacgattctt tagctgccgg gagcagaggc ggaggcggag gcgctgggtt cttgggcaat    60

<210> SEQ ID NO 3
<211> LENGTH: 57
<212> TYPE: DNA
<213> ORGANISM: Artificial sequence
<220> FEATURE:
<223> OTHER INFORMATION: Synthetic oligonucleotide otg7001 (codes for
      GRP).

<400> SEQUENCE: 3
aacgattctt tacatcaggt ggcccacagc ccagtggttt ccgctgccgg gagcaga       57

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide oTG10776

<400> SEQUENCE: 4
ccttccacgg gaagattgta                                                20

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide oTG10781

<400> SEQUENCE: 5
ggggtgtctg tcttcacact                                                20

<210> SEQ ID NO 6
```

<210> SEQ ID NO 6
<211> LENGTH: 26
<212> TYPE: DNA
<213> ORGANISM: Artificial sequence
<220> FEATURE:
<223> OTHER INFORMATION: Synthetic oligonucleotide oTG11065

<400> SEQUENCE: 6
gggaagcttg aggttaacct aagcac                                26

<210> SEQ ID NO 7
<211> LENGTH: 28
<212> TYPE: DNA
<213> ORGANISM: Artificial sequence
<220> FEATURE:
<223> OTHER INFORMATION: Synthetic oligonucleotide oTG11066.

<400> SEQUENCE: 7
gggtctagag ctgccgggag cagaggcg                              28

<210> SEQ ID NO 8
<211> LENGTH: 29
<212> TYPE: DNA
<213> ORGANISM: Artificial sequence
<220> FEATURE:
<223> OTHER INFORMATION: Synthetic oligonucleotide oTG11067.

<400> SEQUENCE: 8
gggctcgagt tatgtttcaa cgtgtttat                             29

<210> SEQ ID NO 9
<211> LENGTH: 24
<212> TYPE: DNA
<213> ORGANISM: Artificial sequence
<220> FEATURE:
<223> OTHER INFORMATION: Synthetic oligonucleotide oTG11068.

<400> SEQUENCE: 9
gtgcccgggg agtttattaa tatc                                  24

<210> SEQ ID NO 10
<211> LENGTH: 31
<212> TYPE: DNA
<213> ORGANISM: Homo sapiens
<220> FEATURE:
<223> OTHER INFORMATION: 0TG11069

<400> SEQUENCE: 10
gcgtctagaa atagtgactc tgaatgtccc c                          31

<210> SEQ ID NO 11
<211> LENGTH: 46
<212> TYPE: DNA
<213> ORGANISM: Homo sapiens
<220> FEATURE:
<223> OTHER INFORMATION: oTG11070

<400> SEQUENCE: 11
gcgctcgagc acaaacgatt ctttagcgca gttcccacca cttcag          46

<210> SEQ ID NO 12
<211> LENGTH: 42
<212> TYPE: DNA
<213> ORGANISM: Mastadenovirus
<220> FEATURE:
<223> OTHER INFORMATION: 0TG7414

<400> SEQUENCE: 12
tagcactcca ttttcgtcgg atccttgaac tgttccagat at        42

<210> SEQ ID NO 13
<211> LENGTH: 43
<212> TYPE: DNA
<213> ORGANISM: Mastadenovirus
<220> FEATURE:
<223> OTHER INFORMATION: oTGA

<400> SEQUENCE: 13
cttataataa gatgagcact ggatccagcc aaaactgaaa ctg        43

<210> SEQ ID NO 14
<211> LENGTH: 45
<212> TYPE: DNA
<213> ORGANISM: Mastadenovirus
<220> FEATURE:
<223> OTHER INFORMATION: oTGB

<400> SEQUENCE: 14
gtagcactcc attttcgtcg gatccaacag ccaaaactga aactg        45

<210> SEQ ID NO 15
<211> LENGTH: 88
<212> TYPE: DNA
<213> ORGANISM: Mastadenovirus
<220> FEATURE:
<223> OTHER INFORMATION: oTG11135

<400> SEQUENCE: 15
cgtcaaatct tataataaga tgagcactca cgttttgtt tttaaacagg gtgttgtagt        60
cgctaacagc caaaactgaa actgtagc        88

<210> SEQ ID NO 16
<211> LENGTH: 64
<212> TYPE: DNA
<213> ORGANISM: Mastadenovirus
<220> FEATURE:
<223> OTHER INFORMATION: oTG10350

<400> SEQUENCE: 16
gtagcactcc attttcgtca agtagagct ccacgttgat actttgaact gttccagata        60
ttgg        64

<210> SEQ ID NO 17
<211> LENGTH: 88
<212> TYPE: DNA
<213> ORGANISM: Mastadenovirus
<220> FEATURE:
<223> OTHER INFORMATION: oTG11136

<400> SEQUENCE: 17
cgtcaaagta gagctccacg ttgatactca cgttttgtt tttaaacagg gtgttgtagt        60
cgctaacagc caaaactgaa actgtagc        88

<210> SEQ ID NO 18
<211> LENGTH: 56
<212> TYPE: DNA
<213> ORGANISM: Mastadenovirus
<220> FEATURE:
<223> OTHER INFORMATION: oTGC

<400> SEQUENCE: 18
ttgaactgtt ccagatattg gggtcagttt gtctttaaca gccaaaactg aaactg    56

<210> SEQ ID NO 19
<211> LENGTH: 48
<212> TYPE: DNA
<213> ORGANISM: Mastadenovirus
<220> FEATURE:
<223> OTHER INFORMATION: oTGD

<400> SEQUENCE: 19
aataagatga gcactttggg tcagtttgtc tattggagcc aaactgcc    48

<210> SEQ ID NO 20
<211> LENGTH: 44
<212> TYPE: DNA
<213> ORGANISM: Mastadenovirus
<220> FEATURE:
<223> OTHER INFORMATION: oTGE

<400> SEQUENCE: 20
ccagatattg gagccaaact gtctttaaca gccaaaactg aaac    44

<210> SEQ ID NO 21
<211> LENGTH: 42
<212> TYPE: DNA
<213> ORGANISM: Mastadenovirus
<220> FEATURE:
<223> OTHER INFORMATION: oTGF

<400> SEQUENCE: 21
tgttccagat attggagcga aactgccttt aacagccaaa ac    42

<210> SEQ ID NO 22
<211> LENGTH: 42
<212> TYPE: DNA
<213> ORGANISM: Mastadenovirus
<220> FEATURE:
<223> OTHER INFORMATION: oTGG

<400> SEQUENCE: 22
atgagcactt tgaactgtgt tagatattgg agccaaactg cc    42

<210> SEQ ID NO 23
<211> LENGTH: 44
<212> TYPE: DNA
<213> ORGANISM: Mastadenovirus
<220> FEATURE:
<223> OTHER INFORMATION: oTGH

<400> SEQUENCE: 23
taagatgagc actttgaacc tttccagata ttggagccaa actg    44

<210> SEQ ID NO 24
<211> LENGTH: 45
<212> TYPE: DNA
<213> ORGANISM: Mastadenovirus
<220> FEATURE:
<223> OTHER INFORMATION: oTGI

<400> SEQUENCE: 24
cttataataa gatgagcact tggtttgtt ccagatattg gagcc    45

<210> SEQ ID NO 25
<211> LENGTH: 48
<212> TYPE: DNA
<213> ORGANISM: Mastadenovirus

```
<220> FEATURE:
<223> OTHER INFORMATION: oTGJ

<400> SEQUENCE: 25
gtcaaatctt ataataagat ggaaactttg aactgttcca gatattgg          48

<210> SEQ ID NO 26
<211> LENGTH: 47
<212> TYPE: DNA
<213> ORGANISM: Mastadenovirus
<220> FEATURE:
<223> OTHER INFORMATION: oTGK

<400> SEQUENCE: 26
ccattttcgt caaatcttat aattttatga gcactttgaa ctgttcc            47

<210> SEQ ID NO 27
<211> LENGTH: 46
<212> TYPE: DNA
<213> ORGANISM: Mastadenovirus
<220> FEATURE:
<223> OTHER INFORMATION: oTGL

<400> SEQUENCE: 27
gcactccatt ttcgtcaaat ctagcaataa gatgagcact ttgaac             46

<210> SEQ ID NO 28
<211> LENGTH: 23
<212> TYPE: DNA
<213> ORGANISM: Mastadenovirus
<220> FEATURE:
<223> OTHER INFORMATION: oTG11102

<400> SEQUENCE: 28
cggttcatcc ctgtggaccg tga                                      23

<210> SEQ ID NO 29
<211> LENGTH: 38
<212> TYPE: DNA
<213> ORGANISM: Mastadenovirus
<220> FEATURE:
<223> OTHER INFORMATION: oTG11103

<400> SEQUENCE: 29
ggcctctaga gttgagaaaa attgcatttc cacttgac                      38

<210> SEQ ID NO 30
<211> LENGTH: 23
<212> TYPE: DNA
<213> ORGANISM: Mastadenovirus
<220> FEATURE:
<223> OTHER INFORMATION: oTG11104

<400> SEQUENCE: 30
ggtattgtac agtgaagatg tag                                      23

<210> SEQ ID NO 31
<211> LENGTH: 23
<212> TYPE: DNA
<213> ORGANISM: Mastadenovirus
<220> FEATURE:
<223> OTHER INFORMATION: oTG11105

<400> SEQUENCE: 31
cgttggaagg actgtacttt agc                                      23
```

<210> SEQ ID NO 32
<211> LENGTH: 38
<212> TYPE: DNA
<213> ORGANISM: Homo sapiens
<220> FEATURE:
<223> OTHER INFORMATION: oTG11106

<400> SEQUENCE: 32
cgcgtctaga ggcgaatagt gactctgaat gtcccctg                      38

<210> SEQ ID NO 33
<211> LENGTH: 45
<212> TYPE: DNA
<213> ORGANISM: Homo sapiens
<220> FEATURE:
<223> OTHER INFORMATION: oTG11107

<400> SEQUENCE: 33
ccactgtaca ataccacttt agggcgcagt tcccaccact tcagg              45

<210> SEQ ID NO 34
<211> LENGTH: 21
<212> TYPE: DNA
<213> ORGANISM: Mastadenovirus
<220> FEATURE:
<223> OTHER INFORMATION: oTG7171

<400> SEQUENCE: 34
atggttaact tgcaccagtg c                                        21

<210> SEQ ID NO 35
<211> LENGTH: 27
<212> TYPE: DNA
<213> ORGANISM: Mastadenovirus
<220> FEATURE:
<223> OTHER INFORMATION: oTG7275

<400> SEQUENCE: 35
gggctcgagc tgcaacaaca tgaagat                                  27

<210> SEQ ID NO 36
<211> LENGTH: 27
<212> TYPE: DNA
<213> ORGANISM: Mastadenovirus
<220> FEATURE:
<223> OTHER INFORMATION: oTG7276

<400> SEQUENCE: 36
ccgctcgaga ctcctccctt tgtatcc                                  27

<210> SEQ ID NO 37
<211> LENGTH: 20
<212> TYPE: DNA
<213> ORGANISM: Mastadenovirus
<220> FEATURE:
<223> OTHER INFORMATION: oTG7049

<400> SEQUENCE: 37
ctgcccggga gtttattaat                                          20

<210> SEQ ID NO 38
<211> LENGTH: 42
<212> TYPE: DNA
<213> ORGANISM: Mastadenovirus
<220> FEATURE:
<223> OTHER INFORMATION: oTG7416

-continued

```
<400> SEQUENCE: 38
tgtttcctgt gtaccgttgg atcctttagt tttgtctccg tt                    42

<210> SEQ ID NO 39
<211> LENGTH: 64
<212> TYPE: DNA
<213> ORGANISM: Mastadenovirus
<220> FEATURE:
<223> OTHER INFORMATION: oTG10352

<400> SEQUENCE: 39
tgtttcctgt gtaccgttta gcatcacggt cacctcgaga ggtttagttt tgtctccgtt    60
taag                                                               64

<210> SEQ ID NO 40
<211> LENGTH: 42
<212> TYPE: DNA
<213> ORGANISM: Mastadenovirus

<400> SEQUENCE: 40
tgtataggct gtgccttcgg atccccaata ttctgggtcc ag                     42

<210> SEQ ID NO 41
<211> LENGTH: 19
<212> TYPE: PRT
<213> ORGANISM: Ad5 fiber Mastadenovirus

<400> SEQUENCE: 41

Leu Ala Pro Ile Ser Gly Thr Val Gln Ser Ala His Leu Ile Ile Thr
 1               5                  10                  15

Arg Phe Asp

<210> SEQ ID NO 42
<211> LENGTH: 19
<212> TYPE: PRT
<213> ORGANISM: Ad3 fiber Mastadenovirus

<400> SEQUENCE: 42

Val Asn Thr Leu Phe Lys Asn Lys Asn Val Ser Ile Asn Val Glu Leu
 1               5                  10                  15

Tyr Phe Asp

<210> SEQ ID NO 43
<211> LENGTH: 8
<212> TYPE: PRT
<213> ORGANISM: Ad5 fiber Mastadenovirus

<400> SEQUENCE: 43

Pro Val Thr Leu Thr Ile Thr Leu
 1               5

<210> SEQ ID NO 44
<211> LENGTH: 8
<212> TYPE: PRT
<213> ORGANISM: Ad3 fiber Mastadenovirus

<400> SEQUENCE: 44

Pro Leu Glu Val Thr Val Met Leu
 1               5

<210> SEQ ID NO 45
```

```
<211> LENGTH: 12
<212> TYPE: PRT
<213> ORGANISM: Artificial Sequence
<220> FEATURE:
<223> OTHER INFORMATION: adaptor encoding a spacer arm of 12 amino acids

<400> SEQUENCE: 45

Pro Ser Ala Ser Ala Ser Ala Ser Ala Pro Gly Ser
1               5                   10

<210> SEQ ID NO 46
<211> LENGTH: 10
<212> TYPE: PRT
<213> ORGANISM: Artificial Sequence
<220> FEATURE:
<223> OTHER INFORMATION: GRP peptide

<400> SEQUENCE: 46

Gly Asn His Trp Ala Val Gly His Leu Met
1               5                   10
```